US012773481B2

(12) United States Patent
Oger et al.

(10) Patent No.: US 12,773,481 B2
(45) Date of Patent: Oct. 27, 2026

(54) URINARY CATHETER KIT

(71) Applicant: B. BRAUN AVITUM AG, Melsungen (DE)

(72) Inventors: Camille Oger, Courville-sur-Eure (FR); Herwig De Roeck, Argenvilliers (FR)

(*) Notice: Subject to any disclaimer, the term of this patent is extended or adjusted under 35 U.S.C. 154(b) by 519 days.

(21) Appl. No.: 18/263,079

(22) PCT Filed: Feb. 10, 2022

(86) PCT No.: PCT/EP2022/053272

§ 371 (c)(1),
(2) Date: Jul. 26, 2023

(87) PCT Pub. No.: WO2022/171749

PCT Pub. Date: Aug. 18, 2022

(65) Prior Publication Data

US 2024/0082464 A1 Mar. 14, 2024

(30) Foreign Application Priority Data

Feb. 12, 2021 (FR) ...................................... 2101386

(51) Int. Cl.
*A61L 29/14* (2006.01)
*A61L 29/08* (2006.01)

(52) U.S. Cl.
CPC ............ *A61L 29/085* (2013.01); *A61L 29/14* (2013.01)

(58) Field of Classification Search
CPC ................................ A61L 29/14; C08L 75/08
See application file for complete search history.

(56) References Cited

U.S. PATENT DOCUMENTS

2009/0012208 A1* 1/2009 Madsen .................. C08L 33/08 523/113
2010/0076546 A1 3/2010 Dias et al.

FOREIGN PATENT DOCUMENTS

| | | | |
|---|---|---|---|
| CN | 106967206 | B | 2/2018 |
| CN | 108430528 | A | 8/2018 |
| EP | 0677299 | A1 | 10/1995 |
| FR | 2840907 | A1 | 12/2003 |
| JP | 2002538939 | A | 11/2002 |
| JP | 2003510134 | A | 3/2003 |
| JP | 2005287845 | A | 10/2005 |
| JP | 2017530747 | A | 10/2017 |
| WO | 2022/171749 | A1 | 8/2022 |

OTHER PUBLICATIONS

ISR-WO dated Mar. 15, 2022 for parent application PCT/EP2022/053272 (WO2022/171749).
Liow Sing Shy et al, "Abstract", M R S Bulletin, vol. 41, No. 07, Jul. 1, 2016 (Jul. 1, 2016), p. 557-566, XP055772955.
CN Office Action from corresponding application No. CN202280011504.6 mailed May 9, 2026.

* cited by examiner

*Primary Examiner* — Deanna K Hall
(74) *Attorney, Agent, or Firm* — Vorys, Sater, Seymour and Pease LLP

(57) ABSTRACT

The present invention is directed to a urinary catheter kit comprising:—an aqueous lubricant composition comprising water and at least one polyether-polyurethane thermogelling copolymer P1, and—a urinary catheter with an external coating of thermogelling copolymer P2 comprising at least ether units.

20 Claims, No Drawings

URINARY CATHETER KIT

FIELD OF THE INVENTION

This invention concerns the field of urinary catheters and, in particular, that of packaged urinary catheters.

PRIOR ART

Urinary catheters are available on the market in various configurations. They are used both in clinical settings and by patients themselves in daily life and in non-sterile environments. The packaging is subject to various requirements that the urinary catheters that have been available to date only partially satisfy.

Catheters are placed either for extended periods of time, e.g. in clinical applications in the case of operations, or intermittently, several times a day, for urination, as in the case of patients with paraplegia.

Catheters normally consist of a tubular part that is thin and flexible, with a rounded end, and, most of the time, have lateral openings in the wall such that the end of the catheter can be inserted into the bladder via the urethra, with the lateral openings allowing urine to pass through the catheter and exit the body. On the opposite end, there is normally a drainage bag or a connector allowing for connection to a drainage bag, usually with a handle at the end of the catheter in order to facilitate the manipulation of the catheter during its insertion into the urethra and its connection to a drainage bag.

Catheters may be coated with a lubricant to ease their insertion into the urethra.

There are generally two types of catheters:

- catheters coated with a dry lubricant that need only be dipped in water to be activated; the water may be directly included in the packaging (which must then be watertight) or in a small watertight sachet that is itself contained inside the packaging,
- (uncoated) catheters stored in a package containing a lubricant composition.

Lubricant-coated catheters may be packaged dry, and must be stored away from moisture until use. This type of kit, comprising water for activation, may cause splashing when the packaging (or the water sachet included in the packaging) is opened by the user.

Additionally, current catheter coatings are generally made of polyvinylpyrrolidone (PVP), which necessitates a UV coating method, rendering the manufacturing process cumbersome.

The second category of catheters (uncoated catheters) avoids this issue of activation and splashing, but the catheter generally does not glide as smoothly as catheters with water-activated coatings.

An object of this invention is thus to provide a ready-to-use urinary catheter kit that is easy to prepare, for a single use, and that is able to glide more smoothly.

SUMMARY OF THE INVENTION

More specifically, this invention concerns a urinary catheter kit comprising:

- an aqueous lubricant composition comprising water and at least one polyether-polyurethane P1 thermogelling copolymer, and
- a urinary catheter with an external coating of thermogelling copolymer P2 comprising at least ether units.

Preferably, the urinary catheter is immersed in the aqueous lubricant composition.

In one embodiment, the thermogelling copolymer P2 comprises at least some ether units and units selected from urethane units, ester units, and mixtures thereof, preferably urethane units.

Preferably, the thermogelling copolymer P1 and the thermogelling copolymer P2 have a viscosity of 5-100 mPa·s, preferably 10-80 mPa·s, at 25° C.

Preferably, the thermogelling copolymer P1 and the thermogelling copolymer P2 comprise poly(ethylene oxide) and poly(propylene oxide) units.

Preferably, the thermogelling copolymer P1 has a poly (ethylene oxide) content of 50-99 wt %, preferably 70-95 wt %, more preferably 75-90 wt %, based on the total weight of the copolymer.

Preferably, the aqueous lubricant composition comprises from 1 to 20% by dry weight, preferably from 2 to 15% by dry weight, more preferably from 3 to 10% by dry weight, of thermogelling copolymer(s) P1, based on the total weight of the aqueous lubricating composition.

In another embodiment of the invention, the aqueous lubricant composition further comprises glycerin, preferably in an amount of from 1 to 30% by weight, preferably from 5 to 25% by weight, more preferably from 10 to 20% by weight, based on the total weight of the aqueous lubricating composition.

In one embodiment, the copolymer coating is applied by dipping and drying the catheter in a composition comprising the thermogelling copolymer P2.

In one embodiment, the thermogelling copolymer coating P2 is applied by extruding a composition comprising the thermogelling copolymer P2.

In one embodiment, the catheter has two layers, preferably identical, of thermogelling copolymer coating P2.

In one embodiment, the catheter is made of olefinic thermoplastic material, and the olefinic thermoplastic material is previously activated by plasma or previously coated with a primer coat before being coated with the thermogelling copolymer.

The invention also concerns the combined use:

- of at least one thermogelling polyether-polyurethane copolymer in an aqueous lubricant composition and
- of at least one thermogelling copolymer comprising at least some ether units, as a coating for a urinary catheter, in a urinary catheter kit in order to reduce the friction coefficient of the catheter.

Other characteristics, variants, and advantages of the implementation of the invention will be better understood from a reading of the following description and examples, which are provided by way of example only.

DETAILED DESCRIPTION OF THE INVENTION

This invention concerns a urinary catheter kit, comprising:

- an aqueous lubricant composition comprising water and at least one thermogelling polyether-polyurethane copolymer P1 and
- a urinary catheter having an external thermogelling copolymer coating P2 comprising at least some ether units.

In the form in which the kit is provided, the urinary catheter is immersed in the aqueous lubricant composition.

Typically, the kit will be provided in a package comprising the urinary catheter, which is immersed in the aqueous lubricant composition.

The two copolymers P1 and P2 are two thermogelling copolymers. The two copolymers P1 and P2 may be identical or different.

'Thermogelling polymer' refers to a polymer that is typically liquid at room temperature (app. 22° C.) and that can transition to the gel state when the temperature increases.

Typically, the thermogelling copolymers P1 and P2 used in the invention have a viscosity at least 10 times greater at 37° C. than at 25° C.

Preferably, the maximum viscosity of the thermogelling copolymers used in the invention will be reached at 37° C.

The two copolymers P1 and P2 may have identical or different viscosities.

Preferably, at least one thermogelling copolymer used in the invention, in particular the copolymer P1, has a viscosity (at 25° C.) of 5-100 mPa·s, preferably 10-80 mPa·s, as measured with a Lamy RM 100 device and its BV1 rotor for a gradient of 50 $s^{-1}$.

In one embodiment, at least one thermogelling copolymer, in particular the copolymer P1, has a viscosity (at 45° C.) of 20-90 Pa·s, preferably 25-75 Pa·s, as measured with a Lamy RM100 device with BV1 rotor for a gradient of 50 $s^{-1}$.

The thermogelling copolymer P1 is a polyether-polyurethane thermogelling polymer, i.e. a polymer comprising ether and urethane units.

The thermogelling copolymer P2 is a copolymer comprising ether units and preferably units selected from urethane or ester units or mixtures thereof. Preferably, the thermogelling copolymer P2 is a copolymer comprising ether and urethane units.

In one embodiment, the thermogelling copolymer P1 and the thermogelling copolymer P2 comprise at least one linear chain comprising ether units.

In one embodiment, the thermogelling copolymer P1 and the thermogelling copolymer P2 comprise poly(ethylene oxide) and poly(propylene oxide) units.

Preferably, the thermogelling copolymer P1 comprises poly(ethylene oxide) and poly(propylene oxide) units linked by urethane moieties.

Preferably, the thermogelling copolymer P2 comprises poly(ethylene oxide) and poly(propylene oxide) units linked by urethane and/or ester moieties, preferably at least some urethane moieties.

In one embodiment, at least one thermogelling copolymer used in the invention, in particular the copolymer P1, has a (ethylene oxide) content of 50-99 wt %, preferably 70-95 wt %, more preferably 75-90 wt %, relative to the total weight of the copolymer.

The thermogelling copolymers (P1 and P2) used in the invention may be as described in document FR2840907. The thermogelling copolymers (P1 and P2) are commercially available, e.g. at PolymerExpert.

The aqueous lubricant composition comprises from 1 to 20% by dry weight, preferably from 2 to 15% by dry weight, more preferably from 3 to 10% by dry weight, of thermogelling copolymer(s) P1, based on the total weight of the aqueous lubricating composition.

In one embodiment, the aqueous lubricant composition further comprises glycerine, preferably in an amount of from 1 to 30% by weight, preferably from 5 to 25% by weight, more preferably from 10 to 20% by weight, based on the total weight of the aqueous lubricating composition.

In one embodiment, the aqueous lubricant composition may further comprise one or more preservatives, preferably in an amount of 0.01-10 wt %, preferably 0.1-5 wt %, more preferably 0.2-3 wt %, relative to the total weight of the aqueous lubricant composition. Preferably, the preservative may be selected from phenoxyethanol, salt, and mixtures thereof.

Typically, the aqueous lubricant composition has a viscosity (at 25° C.) of 100-300 mPa·s, preferably 110-250 mPa·s, more preferably 120-200 mPa.

The aqueous lubricant composition according to the invention may be prepared by mixing the ingredients, preferably at room temperature (RT, 25° C.). In one embodiment, the copolymer, the water, and any preservatives are added simultaneously and then stirred. The glycerine, if any, is then preferably added to the aqueous polymer solution. The mixture is then stirred in order to obtain the aqueous lubricant composition.

The catheter used according to the invention is coated on the outside with a thermogelling copolymer P2. The thermogelling copolymer P2 maybe identical or different to the thermogelling copolymer P1.

In one embodiment, the catheter comprises two layers of thermogelling copolymer P2, and, in this embodiment, the two layers are preferably identical in nature (same thermogelling copolymer P2 for both layers).

The thermogelling copolymer coating may be obtained by a cycle of dipping in a thermogelling copolymer solution, followed by drying. The drying may be air drying or accelerated by laminar flow or by thermal means such as baking, IR heating, etc.

In another embodiment, the thermogelling copolymer coating is applied by extrusion.

When the catheter comprises several layers of thermogelling copolymer coating, each layer may be applied by carrying out a cycle of dipping in a thermogelling copolymer solution, followed by drying, with that cycle being repeated as many times as layers of coating are applied.

In one embodiment, the initial uncoated catheter is made of thermoplastic olefinic (TPO) material.

In one embodiment, the initial uncoated catheter, in particular when it is made of TPO, is previously activated, e.g. by plasma, and/or coated with a primer, before being coated with the thermogelling copolymer. The primer will typically have a chemical affinity with the material of the uncoated catheter, e.g. TPO, which will facilitate the engraftment of the thermogelling copolymer onto the catheter. By way of example only, the primer may comprise a poly(meth)acrylate copolymer.

In one particular embodiment, the catheter is activated by plasma treatment, then the catheter thus activated is dipped into a primer solution and then dried, preferably air-dried, under laminar flow or in a heated environment.

The invention also concerns the combined use of a lubricant composition according to the invention and a catheter coating according to the invention in order to improve the smooth gliding of the catheter. In particular, the friction coefficient is reduced due to the combination of a lubricant composition as defined according to the invention and an outer catheter coating as defined according to the invention.

Thus, the invention concerns the use of at least one thermogelling copolymer in a urinary catheter kit comprising an aqueous lubricant composition and a coated catheter in order to reduce the friction coefficient of the catheter; it is understood that the aqueous lubricant composition comprises at least one thermogelling copolymer P1 and that the coated catheter has at least one (outer) layer of a thermogelling copolymer P2.

The thermogelling copolymer(s) may have one or more of the characteristics defined herein for the copolymers P1 and P2 in relation to the kit according to the invention.

The urinary catheter kit according to the invention allows the urinary catheter to attain a friction coefficient of less than 0.1.

Typically, the kit according to the invention allows the friction coefficient to be reduced by a factor of at least 1.5, preferably at least 2, or at least 2.5, compared to a catheter kit not comprising any thermogelling copolymer (either as a coating or in the lubricant composition).

EXAMPLES

The following examples illustrate the invention without limitation.

Example 1: Description of the Lubricant Compositions

The examples have used lubricant compositions according to the invention and prior-art lubricant compositions.

Preparation of a Lubricant Composition According to the Invention (CLinv):

- mixing water and thermogelling copolymer P1 (EG230® from PolymerExpert, with ether and urethane units) at a temperature below RT, preferably from 2-10° C.,
- optional stirring
- adding glycerine at RT
- stirring.

An aqueous lubricant composition according to the invention was prepared and is described in Table 1 below, indicating the proportions by weight percent relative to the total weight of the aqueous lubricant composition.

TABLE 1

| | CLinv |
|---|---|
| Thermogelling copolymer P1 | 4% |
| glycerine | 15% |
| water | qsp |

A prior-art lubricant composition (CLcomp) was prepared and mainly comprises 80 wt % glycerine and 20 wt % water.

The lubricant composition CLinv has a viscosity (at 25° C.) on the order of 135-175 mPa·s, which makes it possible to avoid splashing the user when opening the urinary catheter kit.

Example 2: Description of the Catheters

The examples used uncoated catheters (Cat-Comp) and catheters coated according to the invention (Cat-inv).

Preparation of a Catheter Coated According to the Invention (Cat-Inv):

- providing an uncoated TPO catheter,
- cleaning the catheter with ethanol,
- plasma treatment of the catheter thus cleaned,
- dipping in a primer bath for app. 5 s,
- air drying or drying with laminar flow for 15-24 h,
- dipping in a thermogelling copolymer P2 bath for app. 5 s,
- air drying or drying with laminar flow for 24 h,
- dipping in a thermogelling copolymer P2 bath for app. 5 s,
- air drying or drying with laminar flow for 24 h.

In this non-limiting example, the coated catheter comprises two layers of thermogelling copolymer P2.

In this example, the thermogelling copolymer P2 comprises poly(ethylene oxide) and poly(propylene oxide) units, and is of the same family as the EG230® polymer from PolymerExpert.

Example 3: Sliding Test

Sliding tests were conducted in order to measure the friction coefficient of the catheters described in example 2 after being immersed (or not) in the lubricant compositions described in example 1.

An FTS 600 REF UTM from Harland Medical Systems was used under the conditions described below.

The sample is placed between the jaws and attached to the traction cell.

The jaws close with a predetermined force Fn, and the traction cell moves upward.

The load cell measures the force Ft opposing the traction.

The sliding behaviour is characterised by the COF calculated as follows:

$$COF = \frac{Ft}{Fn} \quad \text{[math. 1]}$$

where

- Fn is the force applied by the test jaws.
- Ft is the force measured by the load cell to extract the sample from the jaws.

If the COF is elevated, this means that substantial force was required in order to extract the sample from the jaws, which results in substantial friction. Conversely, if the COF is low, this means that little force was required in order to extract the sample from the jaws, i.e. low friction.

The friction coefficient (COF) of a sliding test characterises the sliding behaviour of the sample.

Table 2 describes the characteristics of the test protocol.

TABLE 2

| | | |
|---|---|---|
| Jaw force | 50 | g |
| Crossbar speed (ascent) | 1.0 | cm/s |
| Crossbar acceleration time (ascent) | 1.0 | s |
| Travel distance | 15 | cm |
| Jaw distance | 0.8 | cm |
| Crossbar speed (descent) | 5 | cm/s |
| Crossbar acceleration time (ascent) | 0.1 | s |
| Number of passes | 5 | |

For each kit, the test protocol is as follows:

- attach the catheter to the attachment system (without loosening the screw of the attachment system)
- place the catheter on the moving crossbar
- Check that the moving crossbar and the block are correctly positioned at the graduated protractor
- Start the test following the protocol described in table 2
- Remove the catheter at the end of the resistance test.
- The various kits tested are described in table 3.

TABLE 3

| | Lubricant composition | Catheter |
|---|---|---|
| Kit 1 | CLcomp | Cat-comp |
| Kit 2 | CLcomp | Cat-inv |
| Kit 3 | CLinv | Cat-comp |
| Kit 4 | CLinv | Cat-inv |

Table 4 below shows the friction coefficient for each kit tested.

TABLE 4

| | COF (average of 3 values) |
|---|---|
| Kit 1 | 0.227 |
| Kit 2 | 0.182 |
| Kit 3 | 0.214 |
| Kit 4 | 0.073 |

As shown in table 4, the kit 4 according to the invention has a considerably lower friction coefficient, showing that the sliding behaviour is better with the kit 4 according to the invention. More specifically, the COF is particularly low when the kit uses a thermogelling copolymer both in the aqueous lubricant composition and in the catheter coating. Synergy between the aqueous lubricant composition according to the invention and the catheter coated according to the invention was observed.

The invention claimed is:

1. Urinary catheter kit comprising:

an aqueous lubricant composition comprising water and at least one polyether-polyurethane thermogelling copolymer P1, and a urinary catheter with an external coating of thermogelling copolymer P2 comprising at least ether units.

2. The urinary catheter kit according to claim 1, wherein the urinary catheter kit is a package urinary catheter kit, and wherein the urinary catheter is immersed in the aqueous lubricating composition within the packaged urinary catheter kit.

3. The urinary catheter kit according to claim 1, wherein the thermogelling copolymer P2 comprises at least ether units and units selected from urethane units, ester units, and mixtures thereof.

4. The kit urinary catheter kit according to claim 1, wherein the thermogelling copolymer P1 and the thermogelling copolymer P2 has a viscosity at 25° C. of 5 to 100 mPa·s.

5. The urinary catheter kit according to claim 1, wherein the thermogelling copolymer P1 and the thermogelling copolymer P2 comprise polyethylene oxide and polypropylene oxide units.

6. The urinary catheter kit according to claim 5, wherein the thermogelling copolymer P1 has a polyethylene oxide content of from 50 to 99% by weight based on the total weight of the copolymer.

7. The urinary catheter kit according to claim 1, wherein the aqueous lubricant composition comprises from 1 to 20% by dry weight of thermogelling copolymer(s) P1, based on the total weight of the aqueous lubricating composition.

8. The urinary catheter kit according to claim 1, wherein the aqueous lubricant composition further comprises glycerin in an amount of from 1 to 30% by weight based on the total weight of the aqueous lubricating composition.

9. The urinary catheter kit according to claim 1, wherein the copolymer coating is applied by dipping and drying the catheter in a composition comprising the thermogelling copolymer P2.

10. The urinary catheter kit according to claim 1, wherein the thermogelling copolymer P2 coating is applied by extrusion of a composition comprising said thermogelling copolymer P2.

11. The urinary catheter kit according to claim 1, wherein the catheter has two, preferably identical, layers of thermogelling copolymer P2 coating.

12. The urinary catheter kit according to claim 1, wherein the catheter is made of olefinic thermoplastic material, and the olefinic thermoplastic material is previously activated by plasma or previously coated with a primer coat before being coated with the thermogelling copolymer P2.

13. The urinary catheter kit according to claim 1, wherein the thermogelling copolymer P1 comprises poly (ethylene oxide) and poly (propylene oxide) units linked by urethane moieties, and the thermogelling copolymer P2 comprises poly (ethylene oxide) and poly (propylene oxide) units as ether units.

14. A method of reducing a coefficient of friction of a catheter, the method comprising using:

at least one polyether-polyurethane thermogelling copolymer P1 in an aqueous lubricant composition, and at least one thermogelling copolymer P2 comprising at least ether units, as a coating layer for a urinary catheter, in a urinary catheter kit.

15. The urinary catheter kit according to claim 1, wherein the thermogelling copolymer P2 comprises at least ether units and units selected from urethane units.

16. The urinary catheter kit according to claim 1, wherein the thermogelling copolymer P1 and the thermogelling copolymer P2 has a viscosity at 25° C. of 10 to 80 mPa·s.

17. The urinary catheter kit according to claim 1, wherein the thermogelling copolymer P1 has a polyethylene oxide content of from 70 to 95% by weight, based on the total weight of the copolymer.

18. The urinary catheter kit according to claim 1, wherein the aqueous lubricant composition comprises from 2 to 15% by dry weight, of thermogelling copolymer(s) P1, based on the total weight of the aqueous lubricating composition.

19. The urinary catheter kit according to claim 1, wherein the aqueous lubricant composition further comprises glycerin in an amount of from 1 to 30% by weight, based on the total weight of the aqueous lubricating composition.

20. The urinary catheter kit according to claim 1, wherein the catheter has two identical, layers of thermogelling copolymer P2 coating.

* * * * *